(12) United States Patent
Heilman

(10) Patent No.: US 8,585,595 B2
(45) Date of Patent: Nov. 19, 2013

(54) METHOD AND APPARATUS FOR ALIGNING BONE SCREW HOLES

(75) Inventor: Benjamin P. Heilman, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 71 days.

(21) Appl. No.: 13/014,893

(22) Filed: Jan. 27, 2011

(65) Prior Publication Data

US 2012/0197262 A1 Aug. 2, 2012

(51) Int. Cl.
*A61B 8/00* (2006.01)

(52) U.S. Cl.
USPC ............... 600/437; 606/96; 606/97; 606/104; 600/407

(58) Field of Classification Search
None
See application file for complete search history.

(56) References Cited

U.S. PATENT DOCUMENTS

| | | | |
|---|---|---|---|
| 4,774,959 A | 10/1988 | Palmer et al. | |
| 5,348,009 A | 9/1994 | Ohtomo et al. | |
| 5,806,520 A | 9/1998 | Berger et al. | |
| 5,908,388 A | 6/1999 | Watkin et al. | |
| 6,468,215 B1 | 10/2002 | Sarvazyan et al. | |
| 7,537,566 B2 | 5/2009 | Mano et al. | |
| 7,601,120 B2 | 10/2009 | Moilanen et al. | |
| 2006/0241628 A1* | 10/2006 | Parak | 606/80 |
| 2008/0125653 A1 | 5/2008 | Antich et al. | |
| 2009/0112094 A1 | 4/2009 | Qin et al. | |
| 2010/0137874 A1* | 6/2010 | Kim et al. | 606/102 |

* cited by examiner

*Primary Examiner* — Unsu Jung
*Assistant Examiner* — Saurel J Selkin
(74) *Attorney, Agent, or Firm* — Harness, Dickey

(57) ABSTRACT

A method for estimating at least one of a fastener-hole depth and a fastener length prior to forming a hole in a bone can include selecting a position on a proximal side of a proximal cortical bone layer for forming the hole, transmitting a transmitted wave into the bone from the selected position, and receiving a reflected wave at the selected position after the transmitted wave has been reflected by a distal cortical bone layer. The method can further include determining a distance from the selected position to the distal cortical bone layer based on times at which the transmitted wave is transmitted and the reflected wave is received, and estimating the at least one of the fastener-hole depth and the fastener length based on the distance to the distal cortical bone layer.

21 Claims, 5 Drawing Sheets

METHOD AND APPARATUS FOR ALIGNING BONE SCREW HOLES

FIELD

The following relates to aligning bone screw holes, and more specifically, relates to a gauge for non-invasively estimating bone screw trajectories.

BACKGROUND

The statements in this section merely provide background information related to the present disclosure and does not constitute prior art.

Bone screws and bone plates are used to fix bone fragments when repairing complex fractures. Typically, when inserting a bone screw into a bone, a hole is drilled into a bone at a desired depth and a bone screw is inserted into the hole. To determine if the desired depth has been reached, a surgeon either uses tactile feedback while drilling into the bone or uses a depth gauge after drilling into the bone. Using tactile feedback while drilling into the bone can be inaccurate due to variations in bone density. Using a depth gauge after drilling into the bone can be inaccurate since the drill depth is not determined until after the hole has been drilled.

Thus, there is need for procedures and depth gauges that enable estimating screw trajectories, such as a screw-hole depth or a screw length, prior to forming a hole in a bone. In addition, there is a need for procedures and depth gauges that minimize the amount of fluoroscopy necessary for bone screw insertions, thereby reducing the time and costs required for bone screw insertions.

SUMMARY

A depth gauge for estimating at least one of a fastener-hole depth and a fastener length prior to forming a hole in a bone can include a transmitter, a receiver, a module, and a display. The transmitter can be operable to transmit a wave into a bone from a selected position. The receiver can be operable to receive the wave at the selected position after the wave has been reflected from tissue in the bone. The module can be operable to determine a distance from the depth gauge to the tissue in the bone based on times at which the wave is transmitted and received. The display can be operable to display the distance to the tissue in the bone.

A method for estimating at least one of a fastener-hole depth and a fastener length prior to forming a hole in a bone can include selecting a position on a proximal side of a proximal cortical bone layer for forming the hole, transmitting a transmitted wave into the bone from the selected position, and receiving a reflected wave at the selected position after the transmitted wave has been reflected by a distal cortical bone layer. The method can further include determining a distance from the selected position to the distal cortical bone layer based on times at which the transmitted wave is transmitted and the reflected wave is received, and estimating the at least one of the fastener-hole depth and the fastener length based on the distance to the distal cortical bone layer.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DESCRIPTION OF VARIOUS EMBODIMENTS

The following description is merely exemplary in nature and is not intended to limit the present disclosure, application, or uses. As used herein, the term module refers to an Application Specific Integrated Circuit (ASIC), an electronic circuit, a processor (shared, dedicated, or group) and memory that execute one or more software or firmware programs, a combinational logic circuit, and/or other suitable components that provide the described functionality.

Figure 1:
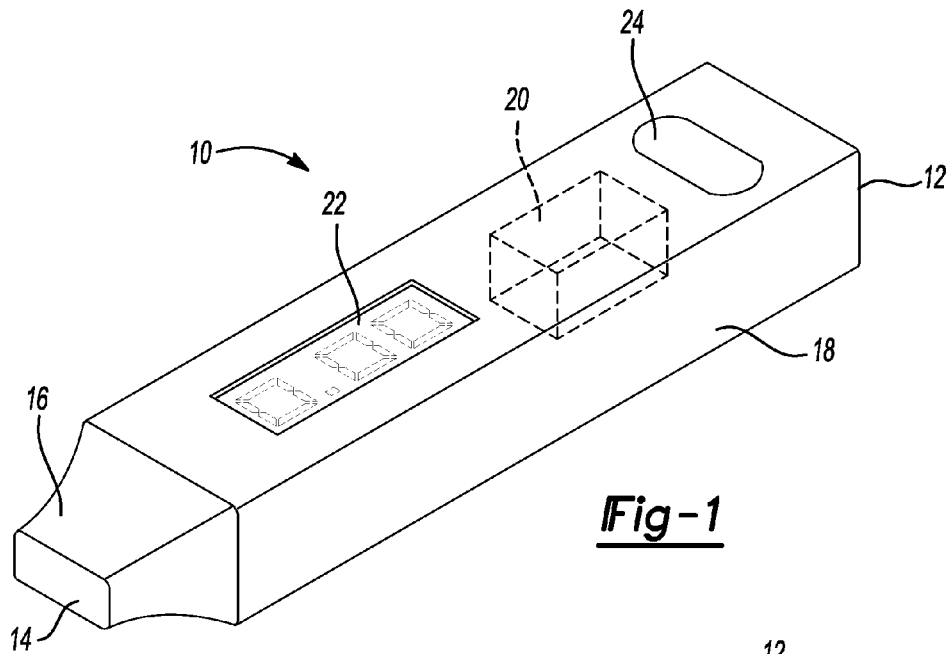
FIG. 1 is a perspective view of a depth gauge according to various teachings of the present disclosure.

Referring to FIG. 1, a depth gauge 10 is illustrated according to various exemplary embodiments of the present disclosure. The depth gauge 10 can be handheld and can include a proximal end 12, a distal end 14, a transducer 16 adjacent to the distal end 14, and a handle 18 extending from the transducer 16 to the proximal end 12. The transducer 16 and the handle 18 can be integral or separate.

The transducer 16 can be trapezoidal, as shown, or can have a different shape. The transducer 16 includes both a transmitter and a receiver, further discussed herein. The transducer 16 can be a transceiver in which the transmitter and receiver are combined and share common circuitry or a single housing. Alternatively, the transducer 16 can be a transmitter-receiver in which the transmitter and receiver are separate.

The handle 18 can be rectangular, as shown, or can have a different shape. The handle 18 can include a module 20, a display 22, and a user interface 24. The module 20 can be in communication with the transducer 16, the display 22, and the user interface 24. The display 22 can display values digitally. The user interface 24 can be a button that allows a user to activate the depth gauge 10. The user interface 24 can be omitted, and the depth gauge 10 can be activated when the transducer 16 detects that the depth gauge 10 is in close proximity with an object.

Figure 2:
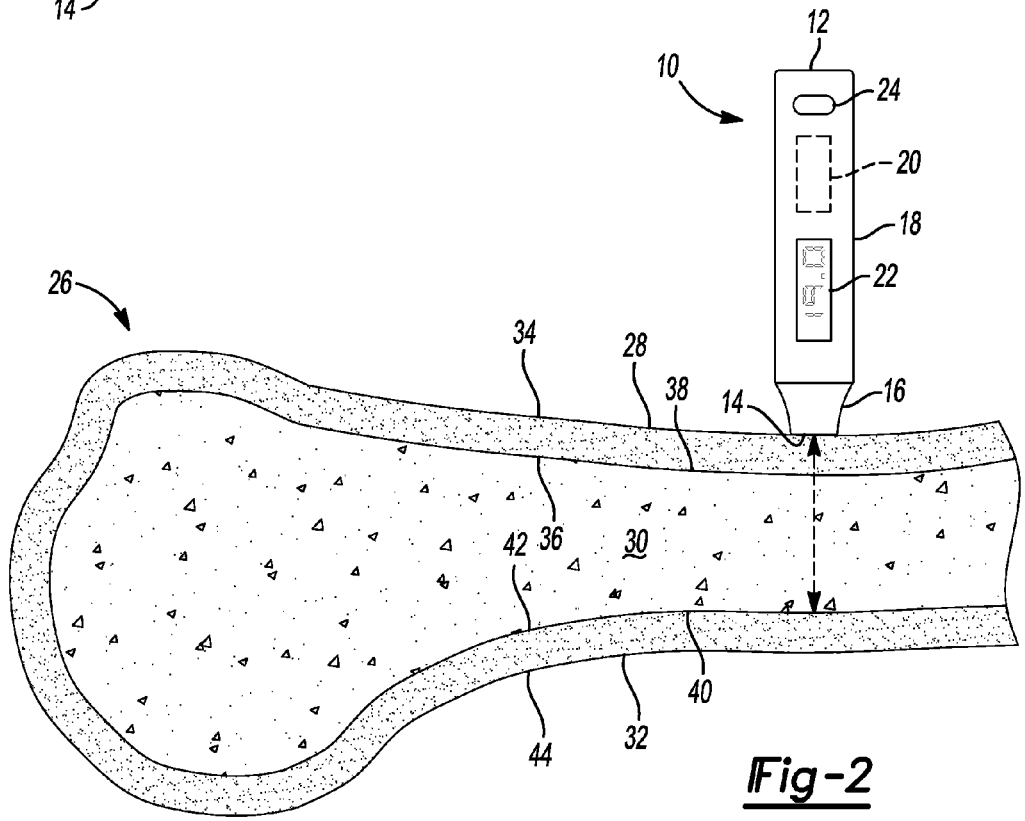
FIG. 2 is a side view of the depth gauge of FIG. 1 indicating a distance from a distal end of the depth gauge to a distal cortical bone.
Figure 3:
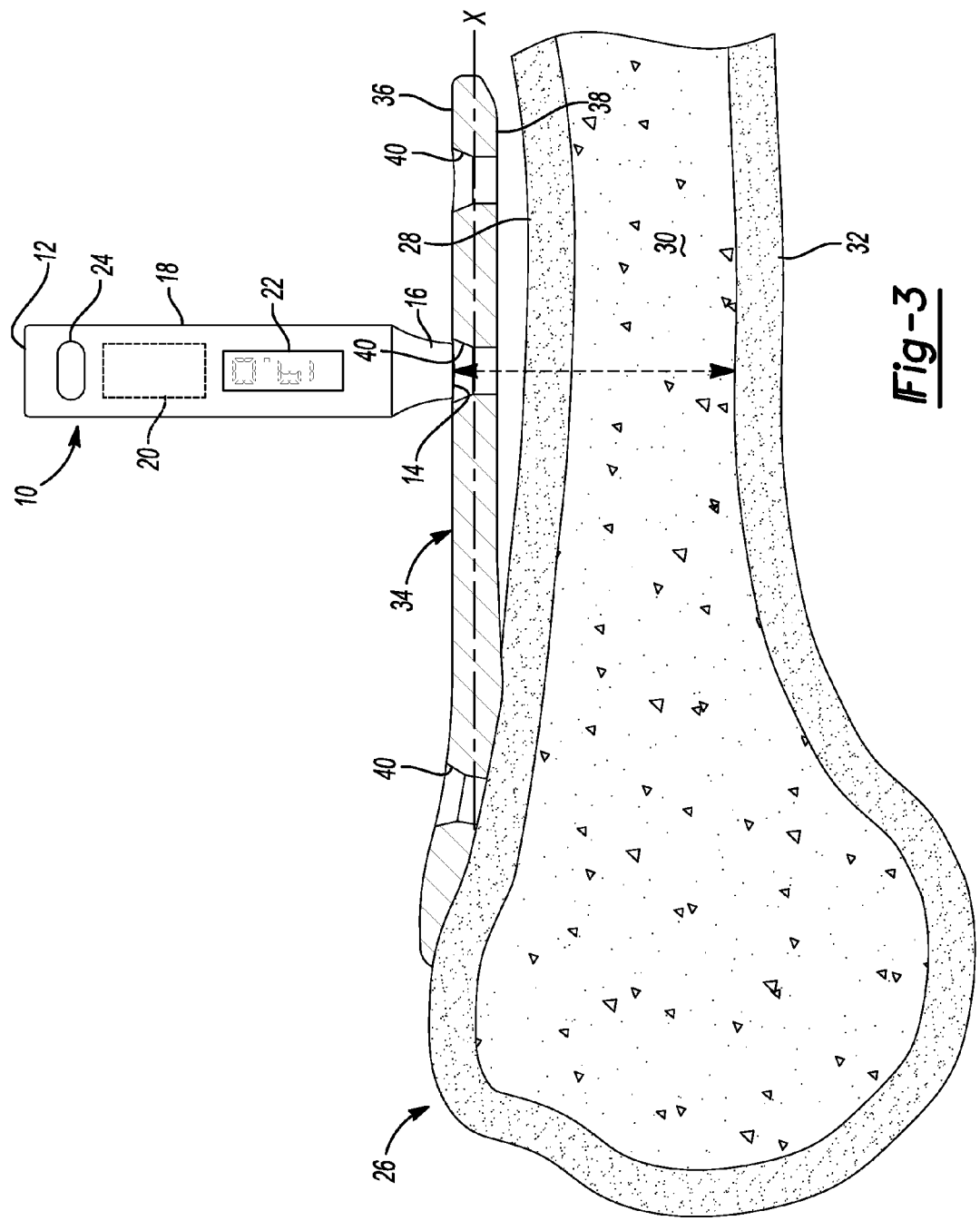
FIG. 3 is a side view of the depth gauge of FIG. 1 positioned normal to a longitudinal axis of a bone plate and indicating a distance from the distal end of the depth gauge to the distal cortical bone.
Figure 4:
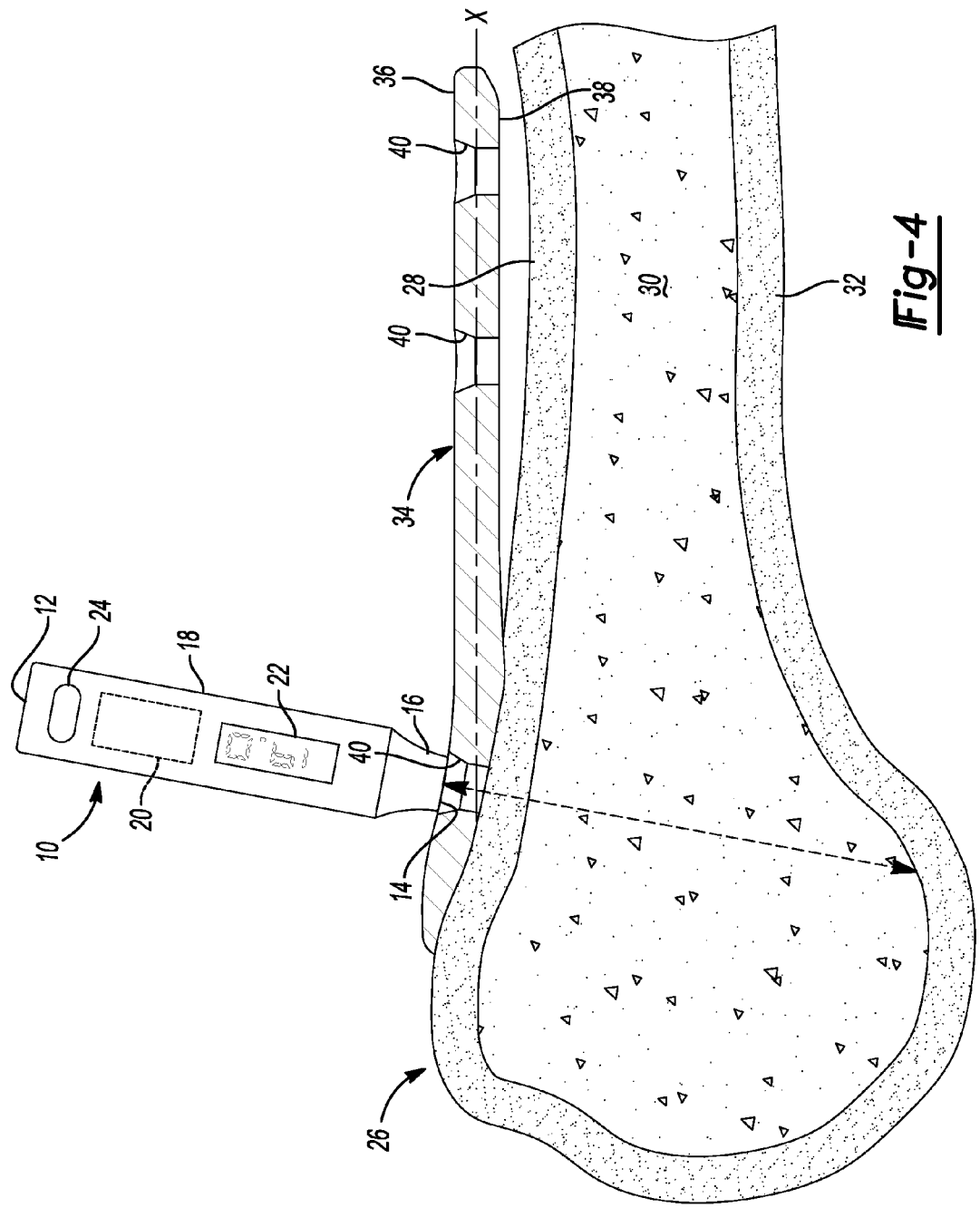
FIG. 4 is a side view of the depth gauge of FIG. 1 angled with respect to the longitudinal axis of the bone plate and indicating a distance from the distal end of the depth gauge to the distal cortical bone.

Referring to FIGS. 2 through 4, operation of the depth gauge 10 will now be described. The depth gauge 10 estimates a hole depth or a length associated with a fastener, such as a screw or a pin, prior to forming a hole in a bone 26. The bone 26 includes a proximal outer cortical bone layer 28, an inner cancellous bone layer 30, and a distal outer cortical bone layer 32. The cortical bone layer 28 includes an outer surface 34 and an inner surface 36. The cancellous bone layer 30 includes a proximal inner surface 38 and a distal inner surface 40. The cortical bone layer 32 includes an inner surface 42 and an outer surface 44. The cortical bone layers 28, 32 are on proximal and distal sides, or opposite sides, of the bone 26. The cancellous bone layer 30 is between the inner surfaces 36, 42 of the cortical bone layers 28, 32.

The depth gauge 10 can be used before fixing bone fragments of the bone 26 to an unbroken portion of the bone 26 using fasteners and/or plates. In this regard, prior to forming holes in the bone 26, a position can be selected on the proximal side of the bone 26 for forming a hole in the bone 26. The hole can be formed before inserting a fastener or while inserting a self-tapping fastener.

The distal end 14 of the depth gauge 10 can be placed at the selected position. The selected position can be directly on the outer surface 34 of the cortical bone layer 28 (FIG. 2). Alternatively, a bone plate 46 having proximal and distal surfaces 48, 50 can be placed on the proximal side of the bone 26, and the selected position can be within or near a plane including the proximal surface 48 of the bone plate 46 (FIGS. 3 and 4). To this end, the bone plate 46 can include holes 52, and the selected position can be at a proximal end of one of the holes 52. The selected position can correspond to a proximal surface of a fastener when the fastener is placed in one of the holes 52 and in the bone 26. The bone 26 and the bone plate 46 can be separated by a gap 54 across which the fastener must extend.

The depth gauge 10 can be positioned normal or perpendicular to a longitudinal axis x of the bone plate 46 when the distal end 14 of the depth gauge 10 is placed at the selected position (FIG. 3), such as over one of the holes 52. Alternatively, the depth gauge 10 can be angled with respect to the longitudinal axis x of the bone plate 46 when the distal end 14 of the depth gauge 10 is placed at the selected position (FIG. 4). In this regard, the depth gauge 10 can be aligned with a desired fastener trajectory.

Actions can be taken to activate the depth gauge 10 using the user interface 24. For example, if the user interface 24 is a button, the user interface 24 can be depressed. In turn, the user interface 24 can activate the module 20, which can activate the transducer 16 and the display 22. Alternatively, the transducer 16 and the module 20 can remain active, and the module 20 can activate the display 22 when the transducer 16 detects an object in close proximity with the depth gauge 10.

With continued reference to FIGS. 2 through 4, the transducer 16 can transmit a wave into the bone 26 from the selected position. The wave can be a wave used in medical imaging, including a sound wave, such as ultrasound or Doppler, a light wave, a radio wave, or a gamma ray. As indicated by the dashed line and the distal arrow, the transmitted wave travels from the distal end 14 of the depth gauge 10, through the cortical bone layer 28 and the cancellous bone layer 30, and to the cortical bone layer 32. The module 20 can instruct the transducer 16 to transmit the transmitted wave and can record a transmit time, or the time at which the wave is transmitted, based on this instruction to the transducer 16.

The inner surface 42 of the cortical bone layer 32 reflects the wave at a normal incidence. As indicated by the dashed line and the proximal arrow, the reflected wave travels from the inner surface 42 of the cortical bone layer 32, through the cancellous bone layer 30 and the cortical bone layer 28, and to the distal end 14 of the depth gauge 10. If the selected position is within or near a plane including the proximal surface 48 of the bone plate 46 (FIGS. 3 and 4), the transmitted and reflected waves can also travel through one of the holes 52 in the bone plate 46.

The transducer 16 can receive the reflected wave at the selected position after the transmitted wave has been reflected by the inner surface 42 of the cortical bone layer 32. The transducer 16 can communicate properties of the reflected wave to the module 20, including frequency, amplitude, and velocity. The module 20 can determine a receipt time, or the time at which the reflected wave is received, based on this communication from the transducer 16.

The transmitted wave can also be reflected by the cortical bone layer 28, the cancellous bone layer 30, and the bone plate 46. To this end, the transducer 16 can receive multiple waves that have been reflected by the bone 26 or the bone plate 46. The module 20 can identify which of the multiple waves has been reflected from the cortical bone layer 32 based on the wave properties and the receipt times. Each of the bone layers 28, 30, and 32 has a different density. The cortical bone layers 28, 32 have a greater density than the cancellous bone layer 30. The module 20 can identify the reflected waves that have been reflected by the cortical bone layers 28, 32 based on the wave properties. In addition, the module 20 can ignore the earlier receipt time of the wave reflected by the cortical bone layer 28, and can use the later receipt time of the wave reflected by the cortical bone layer 32.

The module 20 can determine a distance from the selected position to the cortical bone layer 32 based on the transmit time and the receipt time. The module 20 can determine this distance taking a difference between the transmit time and the receipt time, dividing this difference by two, and multiplying this quotient by a predetermined velocity. The predetermined velocity can correspond to a sound wave travelling through bone in the radial direction (e.g., approximately 3300 m/s).

The module 20 can estimate the fastener-hole depth and/or the fastener length based on the distance to the cortical bone layer 32. The fastener-hole depth and/or the fastener length can be equal to the distance to the inner surface 42 of the cortical bone layer 32. Alternatively, the fastener-hole depth can be equal to a difference between the distance to the inner surface 42 of the cortical bone layer 32 and the distance to the outer surface 34 of the cortical bone layer 28. The module 20 can determine the distance to the cortical bone layer 28 in the same manner that the module 20 determined the distance to the cortical bone layer 32.

The display 22 can display the distance to the cortical bone layer 32, the fastener-hole depth, and/or the fastener length based on communication with the module 20. If the display 22 displays the distance to the cortical bone layer 32 only, the fastener trajectories can be estimated by the user based on the displayed distance. The insertion angle of the fastener with respect to the bone 26 can be estimated based on the angle of the depth gauge 10 with respect to the bone 26.

Figure 5:
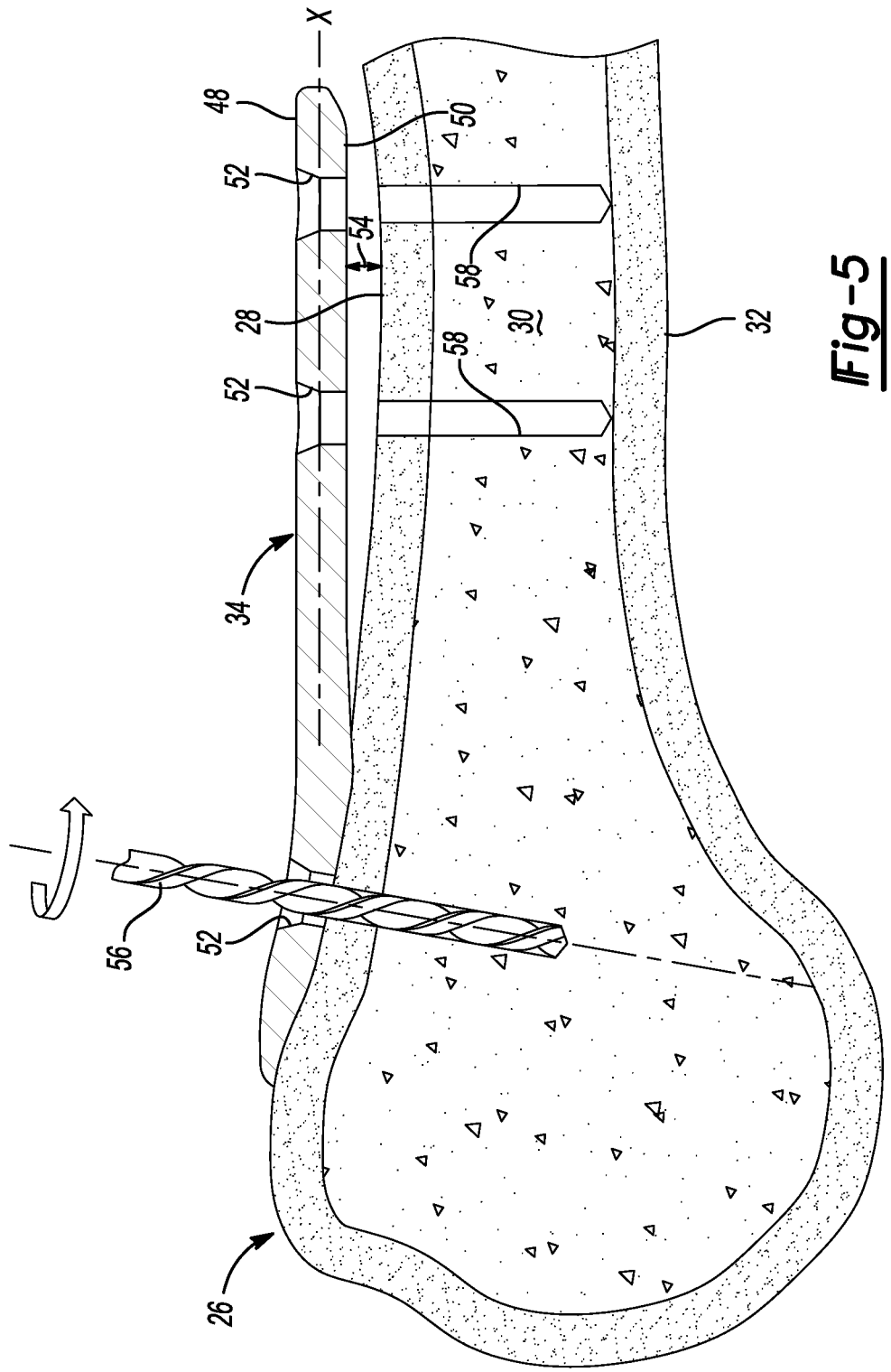
FIG. 5 is a side view of a fastener-hole based on the distance.

Referring to FIG. 5, using a drill bit 56 to drill holes 58 into the bone 26 based on the estimated fastener-hole depth will now be described. The drill bit 56 can be adjusted in a drill (not shown) such that the drill bit extends into the bone 26 to the estimated fastener-hole depth when the drill chuck abuts a proximal surface, such as the outer surface 34 of the cortical bone layer 28 or the proximal surface 48 of the bone plate 46. Alternatively, the drill can have depth markings used to determine when the drill bit has reached the estimated fastener-hole depth.

Figure 6:
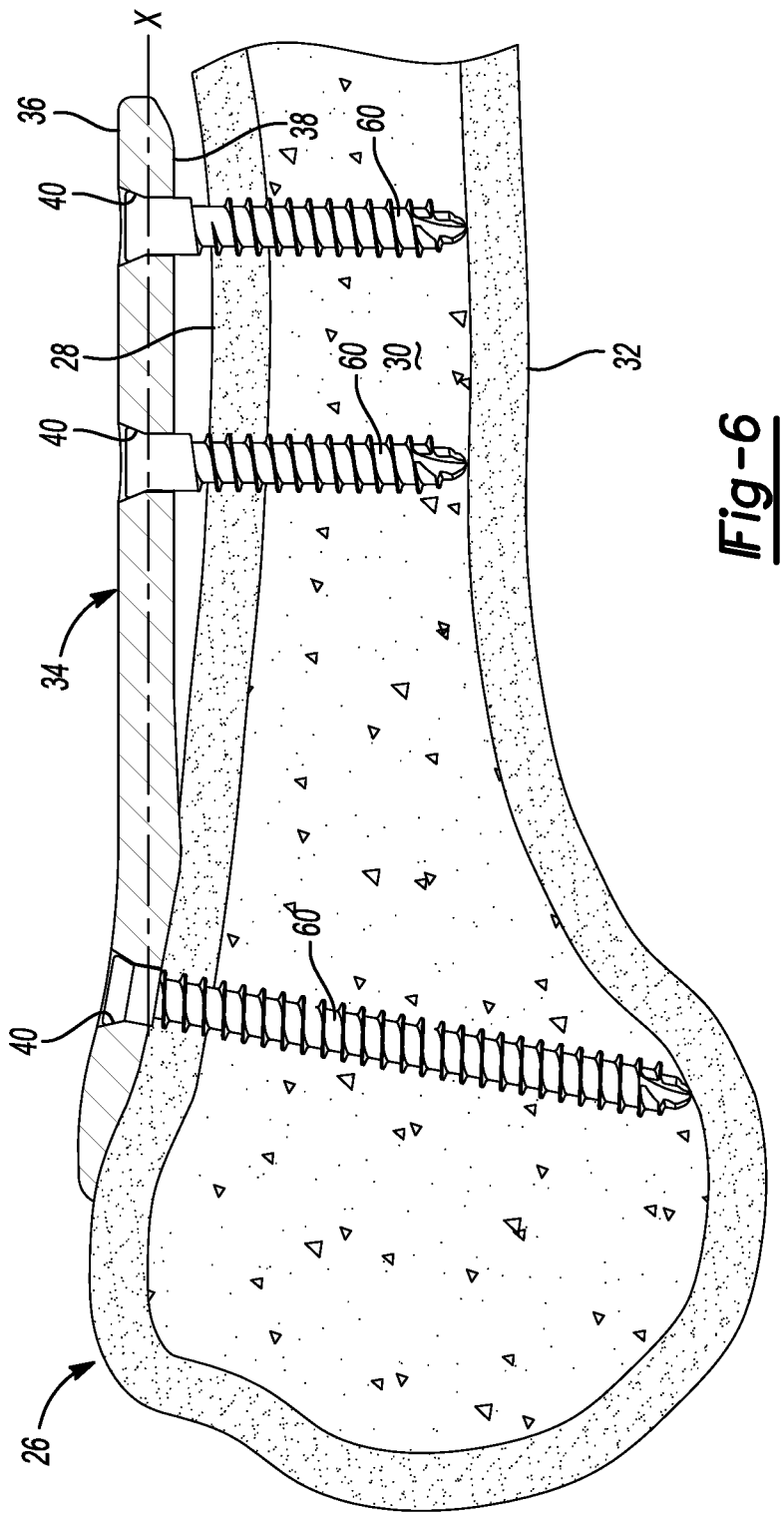
FIG. 6 is a side view of a bone fastener based on the distance.

Referring to FIG. 6, sizing fasteners 60 based the estimated fastener length and inserting the fasteners 60 into the bone 26 will now be described. Sizing the fasteners 60 can include selecting the fasteners 60 from various fasteners having various lengths and/or cutting the fasteners 60. The fasteners 60 can be sized to have a distal end at the inner surface 42 of the cortical bone layer 32, as shown, or can be shorter. The fasteners 60 can be perpendicular to a longitudinal axis of the bone 26 and/or the longitudinal axis x the bone plate 46, or can be angled therefrom. The fasteners 60 can be inserted into the holes 58 in the bone 26, or the fasteners 60 can be self-tapping and inserted into the bone 26 without drilling the holes 58. The depth gauge 10 allows for predetermining the fastener-hole depth and/or the fastener length prior to drilling the holes 58.

The foregoing discussion discloses and describes merely exemplary embodiments of the present disclosure. One skilled in the art will readily recognize from such discussion, and from the accompanying drawings and claims, that various changes, modifications and variations can be made therein without departing from the spirit and scope of the disclosure as defined in the following claims.

What is claimed is:

1. A method for estimating at least one of a fastener-hole depth and a fastener length prior to forming a hole in a bone, comprising:
   selecting a position on a proximal side of a proximal cortical bone layer for forming the hole;
   transmitting a transmitted wave into the bone from the selected position;
   receiving a reflected wave at the selected position after the transmitted wave has been reflected by a distal cortical bone layer;
   determining a distance from the selected position to the distal cortical bone layer based on times at which the transmitted wave is transmitted and the reflected wave is received; and
   estimating the at least one of the fastener-hole depth and the fastener length based on the distance to the distal cortical bone layer.

2. The method of claim 1, wherein the transmitting the transmitted wave includes transmitting an ultrasound wave.

3. The method of claim 1, further comprising displaying the distance to the distal cortical bone layer from the selected position.

4. The method of claim 1, wherein the selected position is on a proximal surface of the bone.

5. The method of claim 1, wherein the at least one of the fastener-hole depth and the fastener length include a thickness of the proximal cortical bone layer and a thickness of a cancellous bone layer.

6. The method of claim 1, wherein the selected position is within a plane including a proximal surface of a bone plate on the proximal side of the bone.

7. The method of claim 6, wherein the bone plate includes holes, and the selected position is at a proximal end of one of the holes.

8. The method of claim 6, wherein the at least one of the fastener-hole depth and the fastener length include a thickness of the bone plate, a thickness of the proximal cortical bone layer, and a thickness of a cancellous bone layer, and a gap between a distal surface of the bone plate and a proximal surface of the bone.

9. The method of claim 1, wherein transmitting the transmitted wave into the bone, receiving the reflected wave at the selected position, and determining the distance to the distal cortical bone layer include using a depth gauge.

10. The method of claim 9, further comprising aligning the depth gauge with a desired fastener trajectory.

11. The method of claim 9, further comprising activating the depth gauge using a user interface included in the depth gauge.

12. The method of claim 1, further comprising:
   forming the hole in the bone based on the estimated fastener-hole depth;
   sizing a fastener based on the estimated fastener length; and
   inserting the fastener into the bone.

13. A method for estimating at least one of a fastener-hole depth and a fastener length prior to forming a hole in a bone, comprising:
   selecting a position on a proximal side of a proximal cortical bone layer for forming the hole;
   positioning a bone plate having at least one hole passing therethrough on the proximal side of the bone;
   transmitting a transmitted wave into the bone from the hole of the bone plate at the selected position;
   receiving a reflected wave at the hole in the bone plate after the transmitted wave has been reflected by a distal cortical bone layer;
   determining a distance from the hole in the bone plate at the selected position to the distal cortical bone layer based on the transmitted and reflected waves; and
   estimating at least one of a fastener-hole depth and a fastener length based on the distance from the hole of the bone plate to the distal cortical bone layer.

14. The method of claim 13, wherein determining a distance further includes determining a distance based on times at which the transmitted wave is transmitted and the reflected wave is received.

15. The method of claim 13, wherein the transmitting the transmitted wave includes transmitting an ultrasound wave.

16. The method of claim 13, wherein the at least one of the fastener-hole depth and the fastener length include a thickness of the bone plate, a thickness of the proximal cortical bone layer, and a thickness of a cancellous bone layer, and a gap between a distal surface of the bone plate and a proximal surface of the bone.

17. The method of claim 13, wherein the transmitting the transmitted wave into the bone, the receiving the reflected wave, and the determining the distance to the distal cortical bone layer includes using a depth gauge and aligning the depth gauge at a desired fastener trajectory.

18. The method of claim 13, further comprising: forming the hole in the bone based on the estimated fastener-hole depth;
   sizing a fastener based on the estimated fastener length; and
   inserting the fastener into the bone.

19. The method of claim 13, further comprising displaying the distance to the distal cortical bone layer from the selected position.

20. A method for estimating at least one of a fastener-hole depth and a fastener length prior to forming a hole in a bone, comprising:
   selecting a position on a proximal side of a proximal cortical bone layer for forming the hole;
   positioning a handheld depth gauge at the selected position on the proximal side;
   aligning the depth gauge along a desired fastener trajectory relative to the proximal side of the proximal cortical bone;
   activating the depth gauge to transmit a transmitted wave into the bone from the selected position at the desired fastener trajectory;
   receiving a reflected wave at the selected position and at the desired fastener trajectory after the transmitted wave has been reflected by a distal cortical bone layer;
   determining a distance from the selected position and at the desired fastener trajectory to the distal cortical bone layer based on times at which the transmitted wave is transmitted and the reflected wave is received; and
   estimating the at least one of the fastener-hole depth and the fastener length based on the distance to the distal cortical bone layer.

21. The method of claim 20, wherein the selected position is within a plane including a proximal surface of a bone plate on the proximal side of the bone.

* * * * *